US00PP08973P

United States Patent [19]

Fuess

[11] Patent Number: Plant 8,973

[45] Date of Patent: Nov. 8, 1994

[54] CHRYSANTHEMUM PLANT NAMED EMPIRE CHEYENNE

[76] Inventor: Janet S. Fuess, 22 Country Club Dr., New York Mills, N.Y. 13417

[21] Appl. No.: 164,403

[22] Filed: Dec. 7, 1993

[51] Int. Cl.[5] ..... A01H 5/00

[52] U.S. Cl. ..... Plt./79

[58] Field of Search ..... Plt. 79, 76

*Primary Examiner*—Howard J. Locker

*Attorney, Agent, or Firm*—Foley & Lardner

[57] ABSTRACT

A new and distinct cultivar of Chrysanthemum plant named Empire Cheyenne, characterized by the combined characteristics of orange-bronze ray florets; fully double flowers with no disc florets; 4.5 to 5.0 cm capitulum diameter; seven week flower response in light/-shade programs; natural season flowering date of September 20, and compact cushion habit.

1 Drawing Sheet

The present invention comprises a new and distinct cultivar of Chrysanthemum, botanically known as *Dendranthema grandiflora,* and referred to by the cultivar name Empire Cheyenne.

Empire Cheyenne is a product of a planned breeding program which had the objective of creating new Chrysanthemum cultivars having compact cushion habit, early flower response in natural season conditions, orange-bronze decorative flowers, free branching habit, and adaptability for both garden and greenhouse cultures.

Empire Cheyenne was originated from a hybridization made by the inventor Janet S. Fuess in a controlled breeding program in New Hartford, N.Y. in September 1988. The female parent was identified as E86-42 and primarily characterized by its pompom flower type and orange ray floret color. The male parent of Empire Cheyenne was Gold Rush, disclosed in U.S. Plant Pat. No. 7,724, and generally characterized by its multiplex daisy inflorescence and its honey bronze ray floret color.

Empire Cheyenne was discovered and selected as one flowering plant within the progeny of the stated parentage by the inventor in August 1989 in a controlled environment in New Hartford, N.Y.

The first act of asexual reproduction of Empire Cheyenne was accomplished when vegetative cuttings were taken from the initial selection in October 1989 in a controlled environment in New Hartford, N.Y. by a technician working under formulations established and supervised by the inventor. Horticultural examination of selected units initiated in August 1990 has demonstrated that the combination of characteristics as herein disclosed for Empire Cheyenne are firmly fixed and are retained through successive generations of asexual reproduction.

Empire Cheyenne has not been observed under all possible environmental conditions. The phenotype may vary somewhat with variations in environment such as temperature, light intensity, and daylength, without, however, any variation in the genotype. The following observations, measurements and comparisons describe plants grown in Oxnard, Calif. under natural outdoor conditions which approximate those generally used in commercial practice.

The following traits have been repeatedly observed and are determined to be basic characteristics of Empire Cheyenne which in combination distinguish this Chrysanthemum as a new and distinct cultivar.

1. Bright, orange-bronze ray florets which exhibit a slightly darker shade at the tips of the florets.
2. Fully double flowers; no disc florets are present.
3. Fully expanded ray florets are approximately 2.0 cm long and 0.8 cm wide, with tri-dentate tips.
4. Average of 220 ray florets per flower.
5. Capitulum is 4.5–5.0 cm in diameter.
6. A 7 week flower response in light/shade programs.
7. Performs well in the outdoor garden, flowering early (September 20) in natural season.
8. Compact cushion habit, making it suitable for production in 4" to 8" containers.
9. Adaptability to either greenhouse or garden cultures.

Of the many commercial cultivars known to the present inventor, the most similar in comparison to Empire Cheyenne is Mirage, disclosed in U.S. Plant Pat. No. 6,388. In comparison to Mirage, Empire Cheyenne has a larger, more truly decorative type flower, an orange flower color (compared to the bronze ray florets of Mirage), a distinctive darkening at the tips of the ray florets, is more freely branching and sizes up better than Mirage, and flowers five day later than Mirage in natural season. The button-like (firm) texture and seven week response time in light/shade programs of Empire Cheyenne are similar to those same characteristics of Mirage.

The accompanying photographic drawings show typical inflorescence and foliage characteristics of Empire Cheyenne, with colors being as nearly true as possible with illustrations of this type. The top illustration is a color photo comprising a top perspective view of Empire Cheyenne grown in a pot. The bottom illustration is a photo comprising a top view showing in greater detail buds and open flowers of Empire Cheyenne.

In the following description color references are made to the The Royal Horticultural Society Color Chart. The color values were determined between 2:00 and 4:00 PM on Sep. 16, 1993 under 4,000 foot candles light intensity at Oxnard, Calif.

Classification:

*Botanical.*—*Dendranthema grandiflora* cv Empire Cheyenne.

*Commercial.*—Garden and greenhouse mum.

INFLORESCENCE

A. Capitulum:
*Form.*—Decorative.
*Diameter across face.*—4.5–5.0 cm.

B. Corolla of ray florets:
*Color (general tonality from a distance of three meters).*—Orange.
*Color (upper surface).*—169A at tip; 170A at mid-floret.
*Color (under surface).*—170A at tip; 162B at mid-floret.

C. Corolla of disc florets: None.

D. Reproductive organs:
*Androecium.*—None.
*Gynoecium.*—Present on ray florets; style 0.4 cm and bifurcated.

PLANT

A. General appearance:
*Height.*—24–28 cm, when grown to maturity in a 7½″ container.

B. Foliage:
*Color (upper surface).*—137B.
*Color (upper surface).*—137C.
*Shape.*—5 lobed.
*Size.*—Approximately 5.6 cm long and 3.5 cm wide.

It is claimed:

1. A new and distinct cultivar of Chrysanthemum plant named Empire Cheyenne, as illustrated and described.

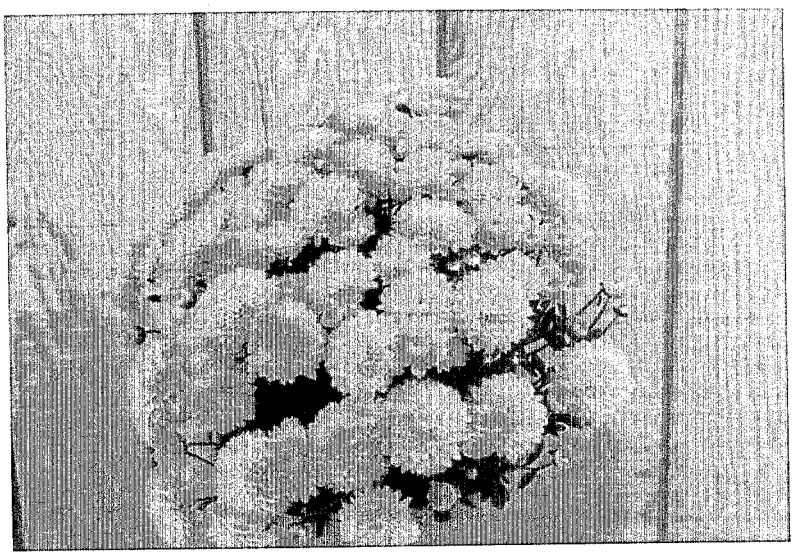
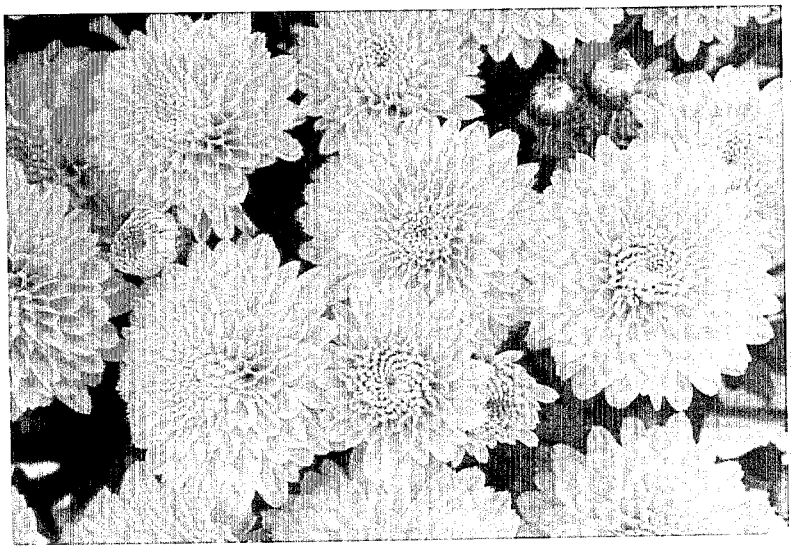

* * * * *